(12) United States Patent
Hashimoto

(10) Patent No.: US 11,439,127 B2
(45) Date of Patent: Sep. 13, 2022

(54) ANIMAL CAPTURING NET

(71) Applicant: Tomoya Hashimoto, Matsubara (JP)

(72) Inventor: Tomoya Hashimoto, Matsubara (JP)

( * ) Notice: Subject to any disclaimer, the term of this patent is extended or adjusted under 35 U.S.C. 154(b) by 0 days.

(21) Appl. No.: 17/002,595

(22) Filed: Aug. 25, 2020

(65) Prior Publication Data
US 2021/0007329 A1 Jan. 14, 2021

Related U.S. Application Data

(63) Continuation of application No. PCT/JP2019/049242, filed on Dec. 16, 2019, which is a continuation-in-part of application No. 16/512,582, filed on Jul. 16, 2019.

(30) Foreign Application Priority Data

Dec. 20, 2018 (JP) .............................. JP2018-238049

(51) Int. Cl.
*A01K 15/04* (2006.01)
*A61D 99/00* (2006.01)
*A61F 5/37* (2006.01)

(52) U.S. Cl.
CPC .............. *A01K 15/04* (2013.01); *A61D 99/00* (2013.01); *A61F 5/37* (2013.01)

(58) Field of Classification Search
CPC ...... A01M 23/00; A01M 31/00; A01M 3/002; A01K 15/00; A01K 15/04; A01K 77/00; A01K 74/00; A61D 99/00; A61F 5/37
See application file for complete search history.

(56) References Cited

U.S. PATENT DOCUMENTS

| | | | | |
|---|---|---|---|---|
| 2,457,922 A | * | 1/1949 | Robinson | A01K 77/00 43/12 |
| 3,318,035 A | * | 5/1967 | Hovland | A01K 77/00 43/12 |
| 3,803,743 A | * | 4/1974 | Nalepka | A01K 97/18 43/4 |
| 4,215,887 A | * | 8/1980 | Boots | E01H 1/1206 294/1.4 |

(Continued)

FOREIGN PATENT DOCUMENTS

| | | |
|---|---|---|
| JP | 11262 | 11/1906 |
| JP | 35-26765 | 10/1960 |

(Continued)

OTHER PUBLICATIONS

International Search Report dated Mar. 3, 2020, issued in counterpart International Application No. PCT/JP2019/049242 (2 pages).

*Primary Examiner* — Peter M Poon
*Assistant Examiner* — Carly W. Lynch
(74) *Attorney, Agent, or Firm* — WHDA, LLP

(57) ABSTRACT

An animal capturing net having a simple mechanism is provided to capture cats or dogs safely and easily. The animal capturing net comprises a net having an upper opening portion, a lower bottom portion, and a prescribed depth D that separates the opening portion and the bottom portion, and a frame that is coupled with the net along an opening edge portion of the net. The frame is constituted to comprise a set of two operating frames facing each other so that they can be operated independently.

3 Claims, 10 Drawing Sheets

(56) References Cited

U.S. PATENT DOCUMENTS

| | | | | |
|---|---|---|---|---|
| 5,605,003 A * | 2/1997 | Krc | ........................ | A01K 77/00 43/12 |
| 7,036,263 B2 * | 5/2006 | Yang | ...................... | A01K 77/00 43/11 |
| 8,857,098 B2 * | 10/2014 | Marks | .................... | A01K 77/00 43/12 |
| 2015/0113852 A1 * | 4/2015 | Kudner | .................. | A01K 77/00 43/11 |

FOREIGN PATENT DOCUMENTS

| | | | | | |
|---|---|---|---|---|---|
| JP | 9-172937 | A | | 7/1997 | |
| JP | H09172937 | A * | 7/1997 | ............. | A01K 74/00 |
| JP | 10-234285 | A | | 9/1998 | |
| JP | 2003-125697 | A | | 5/2003 | |
| JP | 2007-236267 | A | | 9/2007 | |
| KR | 20150028699 | A * | 3/2015 | ............. | A01K 77/00 |

\* cited by examiner

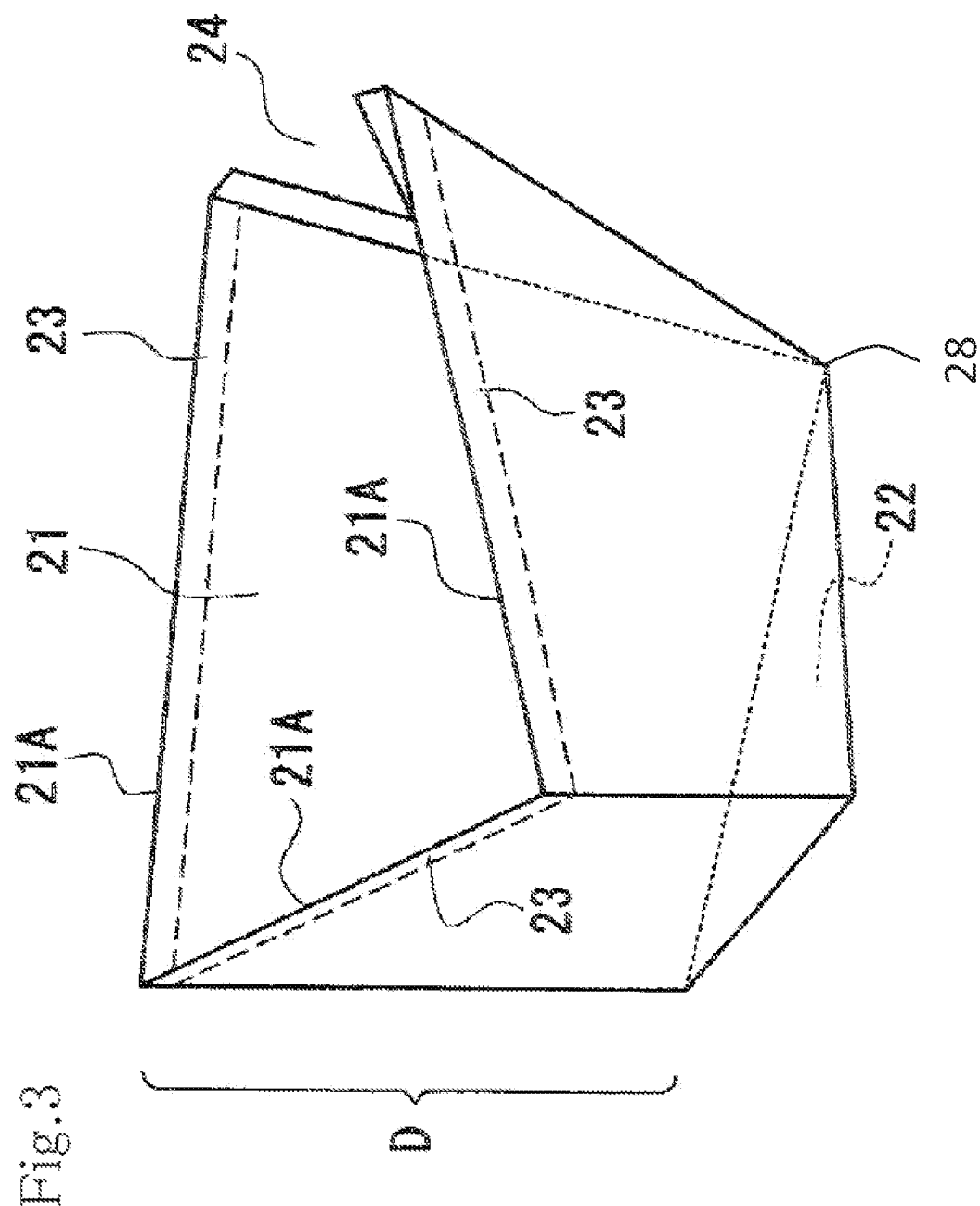

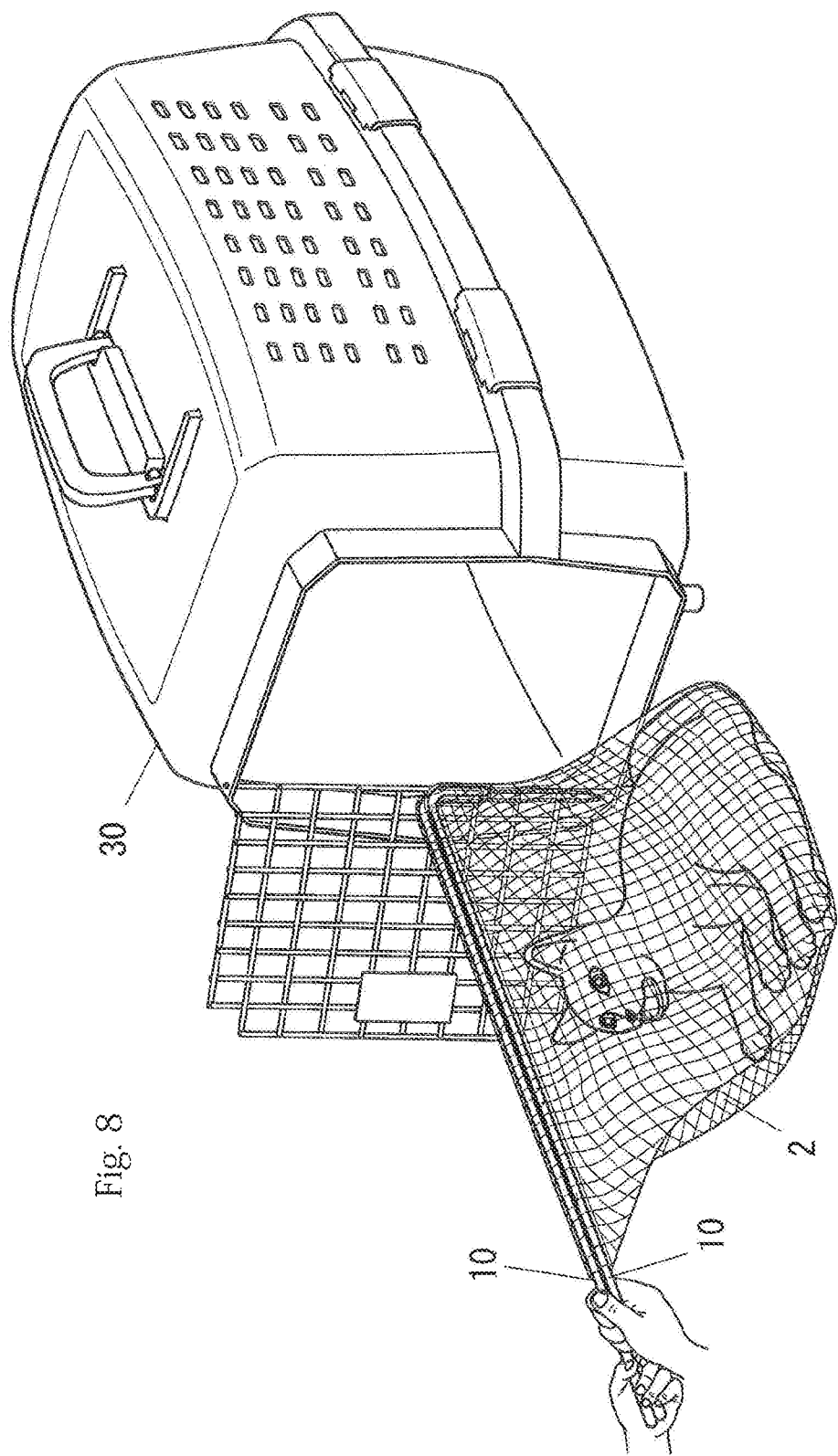

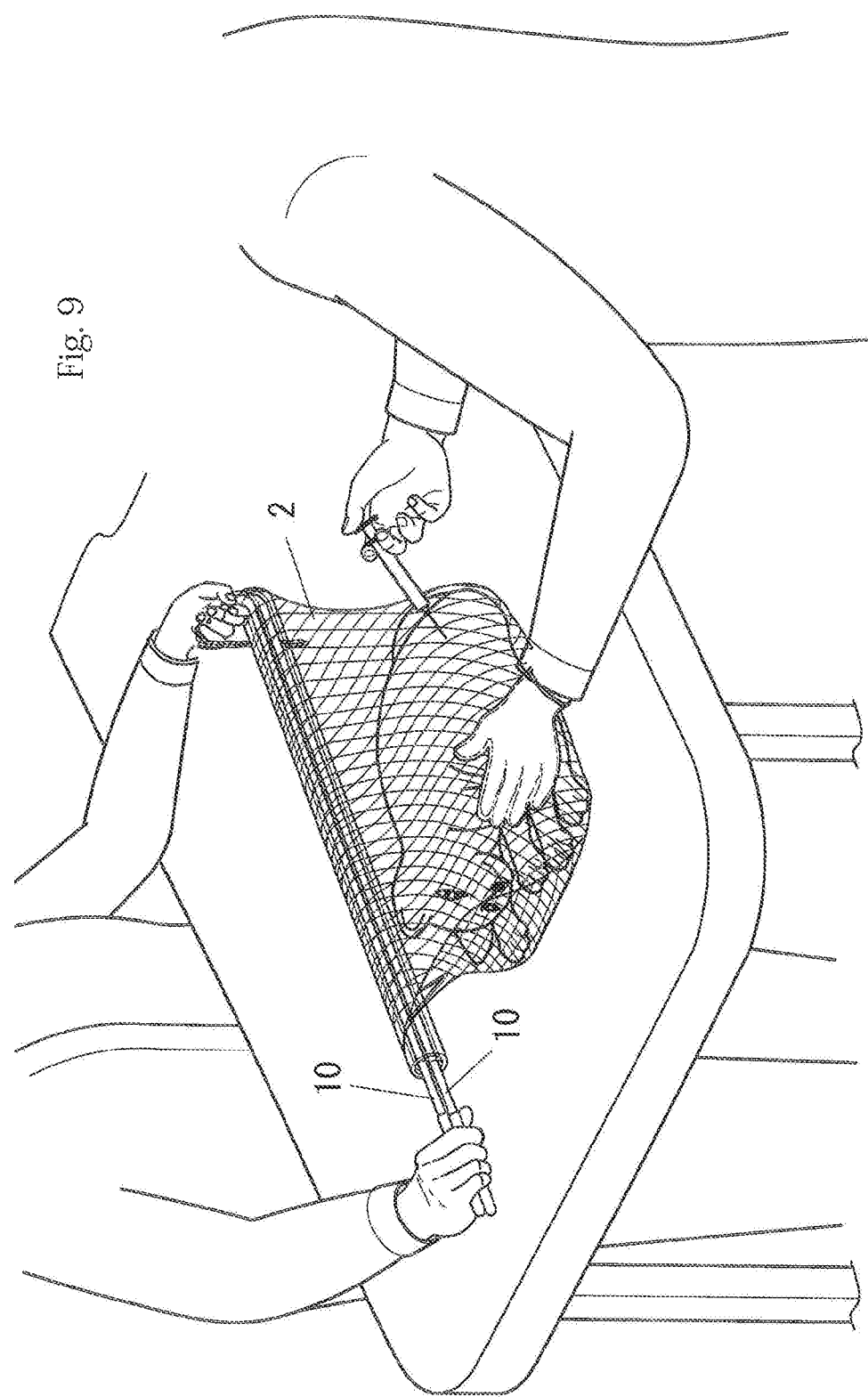

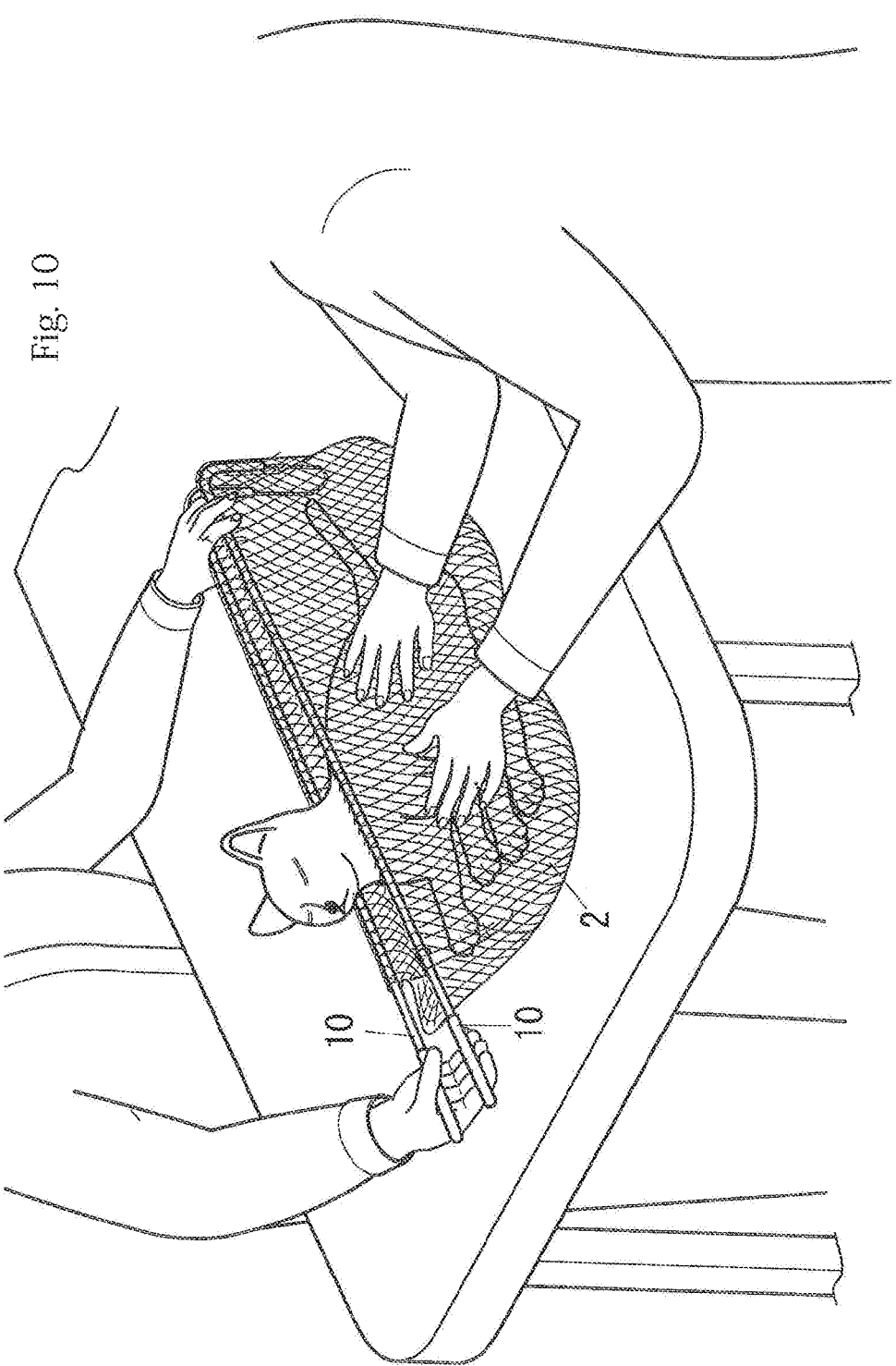

ANIMAL CAPTURING NET

CROSS-REFERENCE OF RELATED APPLICATION

This application is a continuation of international Patent Application No. PCT/JP2019/049242, entitled "Animal Capturing Net" filed on Dec. 20, 2018, which claims priority to and benefit of Japanese Patent Application No. 2018-238049 filed on Dec. 20, 2018, and is a continuation in part of U.S. patent application Ser. No. 16/512,582, entitled "Animal Capturing Net", filed on Jul. 16, 2019, which claims priority to and benefit of Japanese Patent Application No. 2018-238049 filed on Dec. 20, 2018, the entire disclosure of which are incorporated herein by reference.

BACKGROUND OF THE INVENTION

Technical Field

The present invention relates to an animal capturing net. It is possible to capture dogs or cats easily using the animal capturing net of the present invention.

In a veterinary hospital or a beauty parlor for pets, before carrying out treatment or hair trimming, or the like, it is necessary to capture cat or dog that is running around. At this time, it is extremely common that the worker gets scratches on the arms or face because of the cat or dog becoming wild and scratching or biting the worker. Therefore, an animal capturing net is desired that can capture wildly running cats or dogs safely and easily.

For example, if an attempt is made to capture a cat using a capturing machine, some cats will be guarded and will not enter the machine, thereby making catching the animal difficult. Even when an accustomed pet owner tries to catch the pet and put it in a carrying case or a laundry net, or the like, the animal refuses, and the pet owner gets injured. In the case of landing nets for catching fish, although it is possible to put the net over a cat from above, the cat becomes wild thereafter, and the person looking after the pet gets injured while trying to capture it. There is also danger even when cutting the nails.

Under such circumstances, there is the danger that veterinary doctors and persons helping during medical examination could be injured by cats frequently. Even a household cat frequently behaves extremely wild. In the case of stray cats, it could be still worse. It is not possible to catch an animal with something like a laundry net. Cats, in particular, are dangerous as they have mouths with sharp teeth and four limbs with sharp nails, and it is difficult to carry out examination unless attention is paid to all these.

Although leather gloves are sometimes worn to avoid getting injuries, restraining is not easy because of the thickness of the gloves. Even the examination by a veterinary doctor cannot be made if leather gloves are worn. Even restraining is not possible with the weak strength of older people and women. Therefore, it is not possible to protect hands or arms, which get bitten or scratched. Further, with two restraining persons, sometimes the front limbs are restrained by one restraining person, and the rear limbs are restrained by another restraining person, and at the time of keeping pressed or pulling, depending on the respective strengths, accidents of dislocation can be caused. Therefore, examination of stray cats is frequently refused. Also, it may be difficult to safely capture a cat if it is hidden in a narrow space such as under a bed. In addition, it may be difficult to safely capture a cat when it does not come out from a carry case.

The below Patent Document 1 and Document 2 are related to the present application.

PATENT DOCUMENTS

[Patent Document 1] Japanese Unexamined Patent Application Publication No. H09-172937
[Patent Document 2] Japanese Unexamined Patent Application Publication No. 2007-236267

The above Patent Document 1 has the following descriptions:

A capturing tool that captures by covering the target at the front by a net that is widened by stretching and extending by rotating towards the front from above the head.

The present invention is explained in the following with reference to the drawings. FIG. 1 is an outline diagram of the capturing tool of the present invention. Sliding tools 7 provided on both sides of a triangular net 1 are converged and stored in the rail 2. The metal plate 4 has holes for adjusting the angle of the rail, four such holes are provided, and this is a figure showing as an example the stretching and extending the net by 60 degrees. The handle 3 is extended and held in the condition in which the net is converged and stored inside the rail 2, and the net is stretched and extended at 60 degrees towards the front by the centrifugal force of the weight 6 at the tip of the net 2 by rotating the capturing tool from the rear to the front above the head.

The capturing tool prepared in this manner is set to an angle of 90 degrees, the sliding tool is stored in the rail groove towards the handle, the handle is extended and held with both hands, the net gets beautifully widened when the handle is rotated from the rear above the head towards the front, and covered the person at the front.

The above Patent Document 2 has the following descriptions:

A capturing tool having a mechanism for opening and closing the opening of the net.

Said handheld type capturing tool 1 is provided with, a net driving means 12 that supplies drive force for automatically changing the shape of said net 3 from the open state of said opening 4 to the closed state, and an operating member 13 that makes it possible to control said net driving means 12 at the rear end portion 2a of said stick 2.

In the present embodiment, as said net driving means 12 has been provided a coil type tension spring that always applies a restoring force to said net 3 to the closed state of said opening 4. In concrete terms, inside the hollow of said stick 2 has been inserted as said operating member an operating rod 14 that is movable in the front and back direction. The front end portion 14a of this operating rod 14 is coupled with the central portion in the length direction of said movable frame member 7. On the other hand, the rear end portion 14b of said operating rod 14 is positioned more towards the front than the rear end portion 2b of said stick 2. Further, said tension spring 12 has been placed between a plug bolt 17 that closes the rear end opening of the grip pipe 15 forming the rear end of said stick 2 and said rear end portion 14b of said operating rod 14. This tension spring 12 is constantly pressing said operating rod 14 towards the rear of said stick 2. As a result, said operating rod 14 is normally held at a position where said movable frame member 7 is abutting against said extended portion 9 of said fixed frame member 6. Therefore, under normal conditions, said opening 4 of said net 3 is held in the fully closed state due to the pressing force of said tension spring 12.

DISCLOSURE OF THE INVENTION

Problem(s) to be Solved by the Invention

The technology of the above Patent Document 1 is one, in which a net that is stretched and extended by rotating the capturing tool from above the head to the front covers the animal at the front, thereby capturing the animal. In order to realize this, a complicated structure is required such as a sliding member that makes the rail slide, or a weight, or the like. Once the net is stretched and extended, the operation of returning it to the original state is required by hauling in the net. Since the net cannot be used unless it is returned to the original state, when capturing fails, it is not possible to promptly move on to the next capturing operation. In the meantime, the animal is acting wild, and there is the possibility of the operator getting scratched.

The technology of the above Patent Document 2 is one having a mechanism, with which it is possible to open or close the opening of the net. In order to realize this, a complicated structure becomes necessary such as inserting an operating rod inside the hollow of the stick so as to be free to move in the front and back direction, or to use a tension spring that constantly pushes with a force to restore the open net to the closed state, or the like.

The present invention was made in order to solve the above problems in the above Patent Document 1 and Document 2 with the following objectives: (1) to provide an animal capturing net with a simple mechanism and with which it is possible to safely and easily capture a cat or a dog; and (2) to provide an animal capturing net that can keep the state as capturing a cat or a dog.

Means for Solving the Problem

The animal capturing net of the presented invention has the following configuration to achieve the objective described above. The animal capturing net is provided with, a net having an upper opening portion, a lower bottom portion, and a prescribed depth that separates the opening portion and the bottom portion, and a frame that is coupled with the net along the opening edge portion of the net. Here the frame is constituted to comprise a set of two operating frames that can be operated independently, the operating frame comprises a gripping portion, and a coupling portion that extends from the gripping portion and couples with the opening edge portion of the net, the bottom portion of the net has a shape having an apex in the direction towards the gripping portion of the operating frame, and the opening portion has a shape having a side in a direction towards the gripping portion of the operating frame.

The animal capturing net of the present invention has the following configuration in addition to the previous configuration disclosed in the above paragraph. The operating frame comprises a gripping portion, and a coupling portion that extends from the gripping portion and couples with the opening edge portion of the net, the bottom portion of the net has a shape having an apex in the direction towards the gripping portion of the operating frame, and the opening portion has a shape having a side in a direction towards the gripping portion of the operating frame.

The animal capturing net of the presented invention has the following configuration. The frame has the tips of the coupling portions of the two operating frames respectively formed in the shape of hooks.

The animal capturing net of the present invention has the following configuration in addition to the previous disclosed in the above paragraphs. The frame is configured such that it has tips of the two operating frames coupled to each other by a string body.

Effects of the Invention

An animal capturing net of the present invention is provided with a net and a frame. The net has a prescribed depth separating the upper opening portion and the lower bottom portion. The frame is coupled with the net along the opening edge portion of the net. The frame is constituted to comprise a set of two operating frames. The operating frame has a gripping portion and a coupling portion. The coupling portion extends from the gripping portion, and is coupled with the opening edge portion of the net.

Therefore, the net is put from above on the animal while gripping respectively the gripping portions of the set of two operating frames with both hands, when the coupling portion is open and the bottom portion of the net is above. In this state, it is possible to capture an animal by covering the animal with the net by closing the coupling portion by operating the operating frame. After capturing the animal, in the state, in which the opening portion is closed by bringing together the two operating frames, if the top and bottom of the net are inverted, it will be possible to restrain that animal as it is. In that state, it is possible to carry out examination, blood sample collection, body examination, nail clipping, or the like. It becomes extremely easy to carry out, for example, examinations, or the like by a veterinarian.

The animal capturing net of the present invention has the frame, where the operating frame has a gripping portion and a coupling portion. The coupling portion extends from the gripping portion, and is coupled with the opening edge portion of the net. The shape of the bottom portion of the net has an apex in the direction towards the gripping portion of the operating frame. Since the shape of the opening portion of the net has a side towards the gripping portion of the operating frame, it is possible to open and close the coupling portion widely, and it is easy to put the net over an animal. Further, the shape of the bottom portion of the net has an apex in the direction towards the gripping portion of the operating frame. Because of this, space for the animal to move becomes small when the net is put over it, the movement of the animal is restricted, and the animal can be captured smoothly.

In the animal capturing net of the present invention, the tips of the coupling portion of the two operating frames are respectively formed in the shape of hooks. Therefore, the net is put on the animal from above while gripping respectively the gripping portions of the set of two operating frames with both hands, when the coupling portion is open and the bottom of the net is above. In this state, it is possible to capture an animal by covering the animal with the net by closing the coupling portion by operating the operating frame.

At this time, since the tips of the coupling portions of the two operating frames have respectively been formed with the shapes of hooks, when the frame is put over the animal from above and the coupling portion is closed, the hook-shaped portions get caught with the leg of the animal, thereby stopping the movement of the animal and making it possible to cover the animal easily with the net and to capture the animal.

After capturing the animal, in the state, in which the opening portion is closed by bringing together the two operating frames, if the top and bottom of the net are inverted, it will be possible to restrain that animal as it is. In that state, it is possible to carry out examination, blood sample collection, body examination, nail clipping, or the like. It becomes extremely easy to carry out, for example, examinations, or the like by a veterinarian.

In the animal capturing net of the present invention, in the frame, the tips of the two operating frames are coupled with each other by a string body. Because of this, when putting the net over an animal, the opening shape of the net becomes stable along the string body, and it is easy to put the net over an animal.

BRIEF DESCRIPTION OF THE DRAWINGS

FIG. 3 is a perspective view diagram showing an example of the net.

FIG. 8 is a schematic illustration showing the third step of the operation of the present invention.

FIG. 9 is a schematic illustration showing the fourth step of the operation of the present invention.

FIG. 10 is a schematic illustration showing another example to stable the animal by the operation of the present invention.

MODES FOR CARRYING OUT THE INVENTION

Next, the embodiments of the present invention are described in detail below.

Overall Configuration

Figure 1:
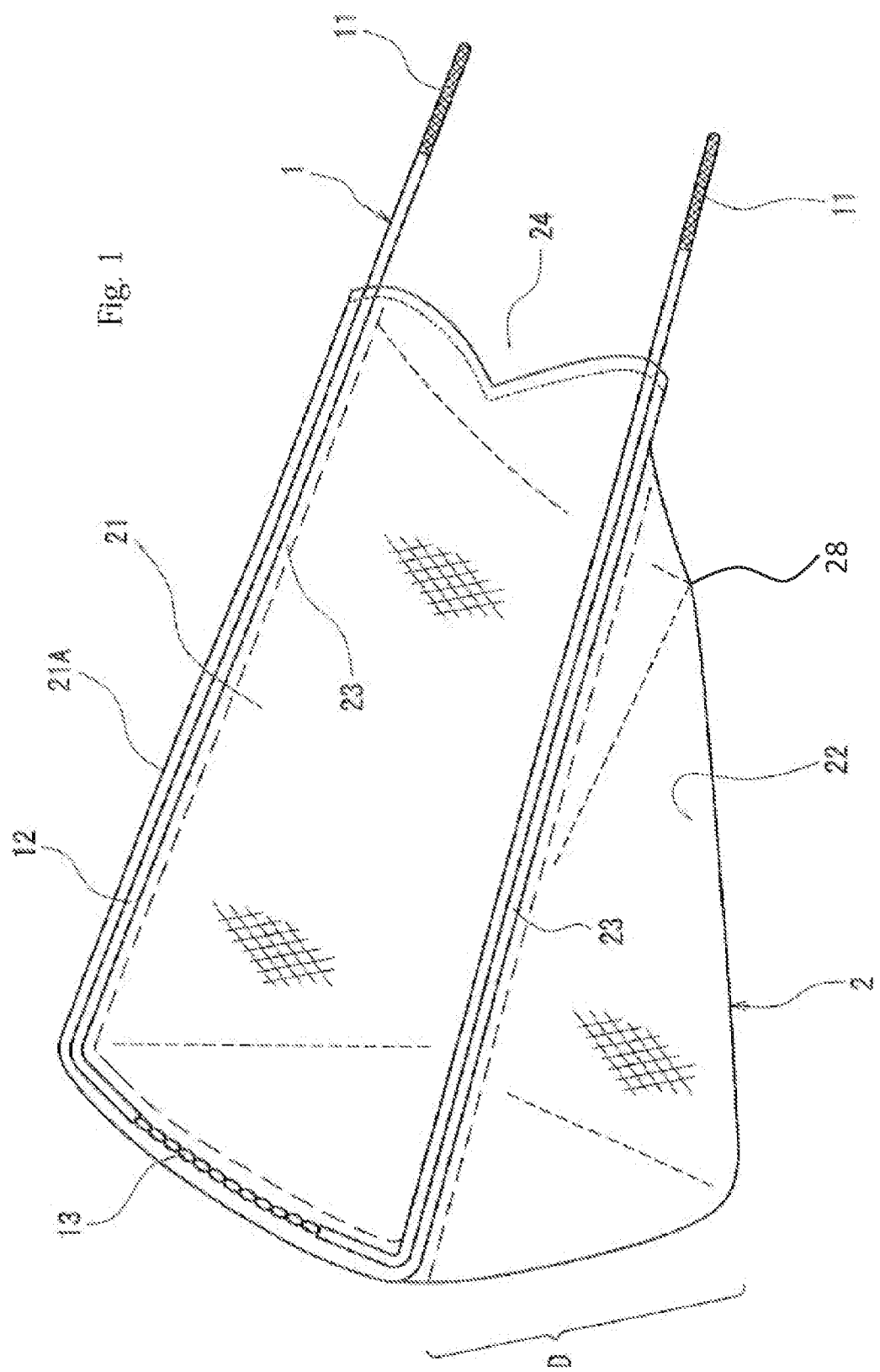
FIG. 1 is a perspective view diagram showing a preferred embodiment of the present invention.

FIG. 1 is a perspective view diagram showing a preferred embodiment of the present invention.

This animal capturing net is provided with a frame 1 and a net 2. The net 2 comprises an upper opening portion 21, a lower bottom portion 22, and a prescribed depth D that separates the opening portion 21 and the bottom portion 22. The frame 1 is coupled with the net 2 along the opening edge portion 21A of the net 2.

Frame

Figure 2:
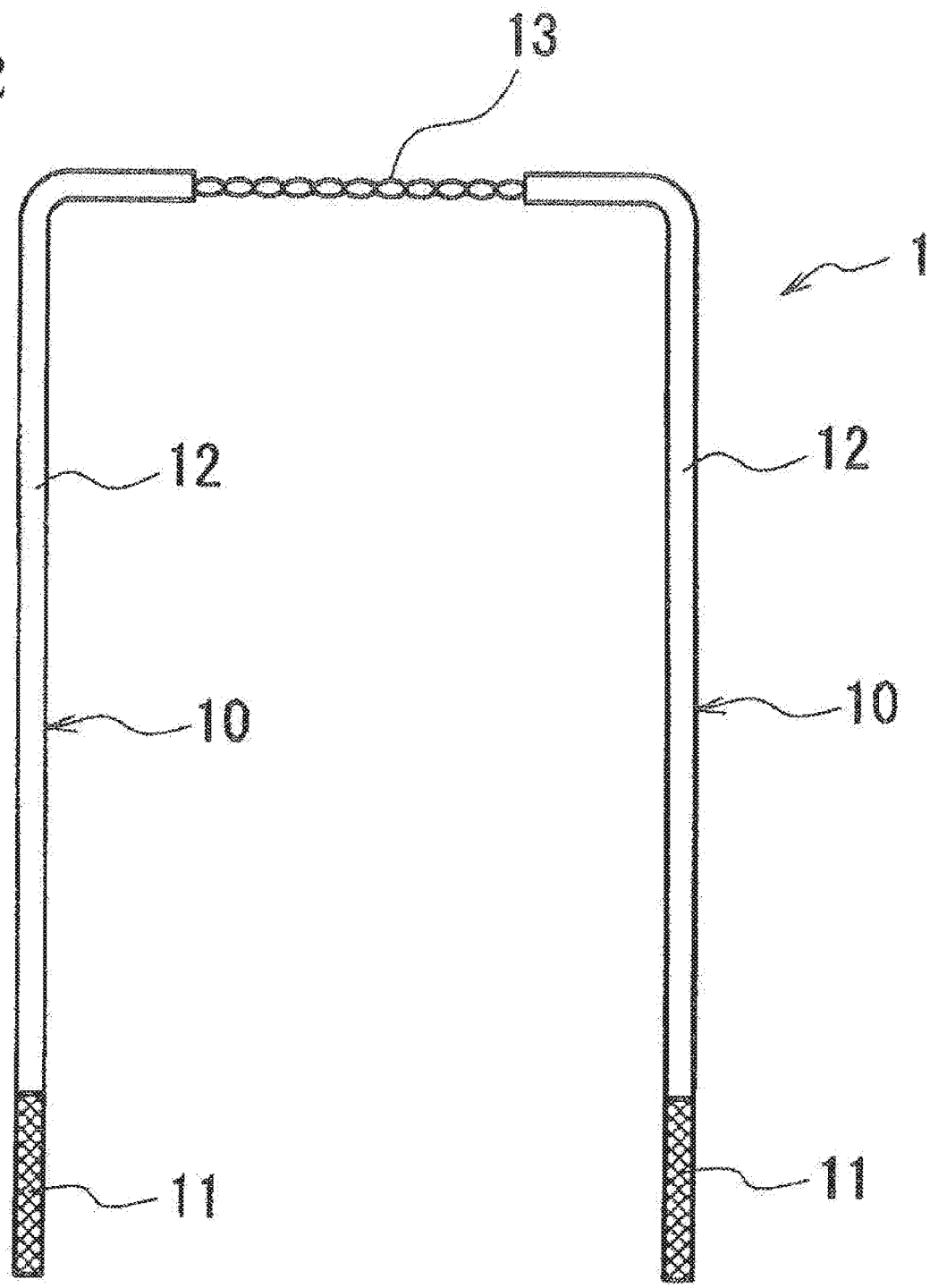
FIG. 2 is a diagram showing an example of the frame.

FIG. 2 is a diagram showing one example of the frame 1.

This frame is constituted to comprise a set of two operating frames 10.

The operating frame 10 can be prepared, for example, using a pipe material made of a metal such as aluminum or the like.

The operating frame 10 is provided with a gripping portion 11, and a coupling portion 12 that extends from the gripping portion 11 and is coupled with the opening edge portion 21A of the net 2.

The gripping portion 11 is one that is operated by the user by gripping in one hand, and it is possible to carry out slipping prevention treatment in order to improve the ease of operation. The slipping prevention treatment can be realized, for example, by covering with a grip made of rubber, or by winding a slipping prevention tape.

The coupling portion 12 extends from the gripping portion that a user grips over a prescribed length, for example, towards the front of the user. In this example, the tips of the two operating frames 10 have respectively been formed by bending into hook shapes. In addition, the tips of the two operating frames 10 are mutually coupled by a string body 13. As for the string body 13, it is possible to use, for example, a chain made of a metal such as aluminum or the like.

Net

Figure 4A:
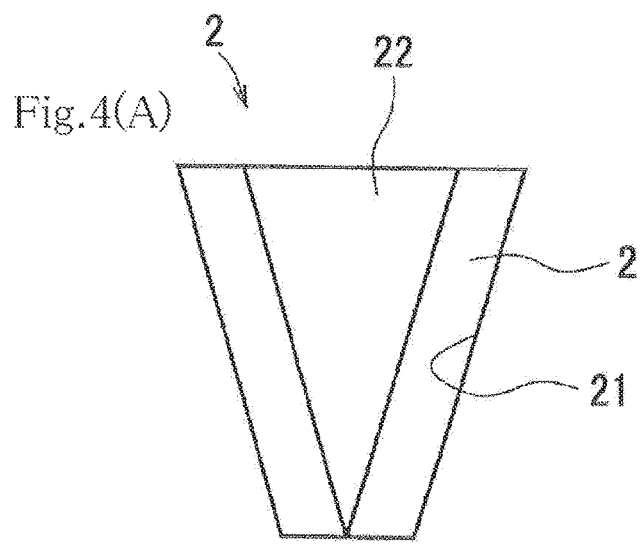
FIG. 4(A) is a diagram showing the net in the plan view.
Figure 4B:
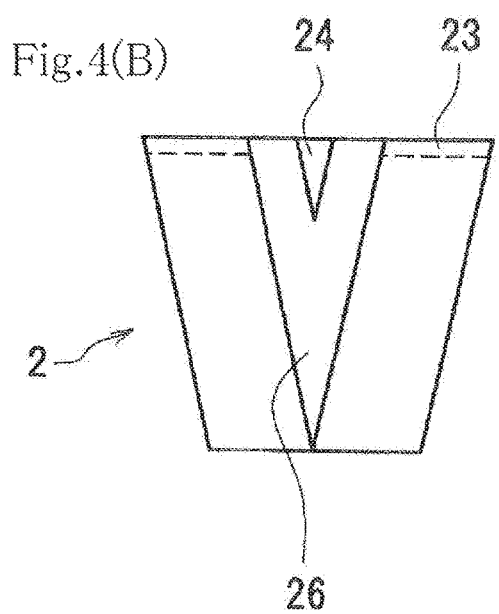
FIG. 4(B) is a diagram showing the net in the front elevation view.
Figure 4C:
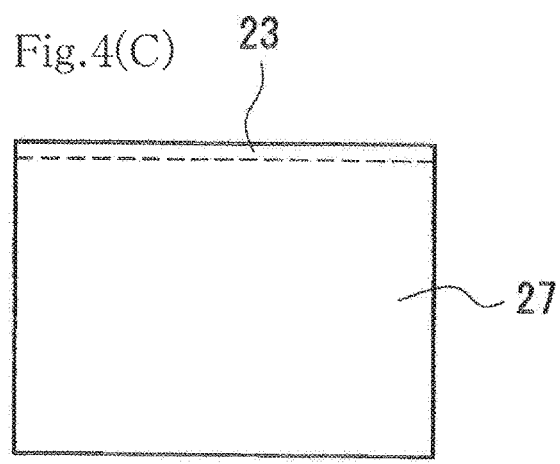
FIG. 4(C) is a diagram showing the net in the side view.
Figure 5:
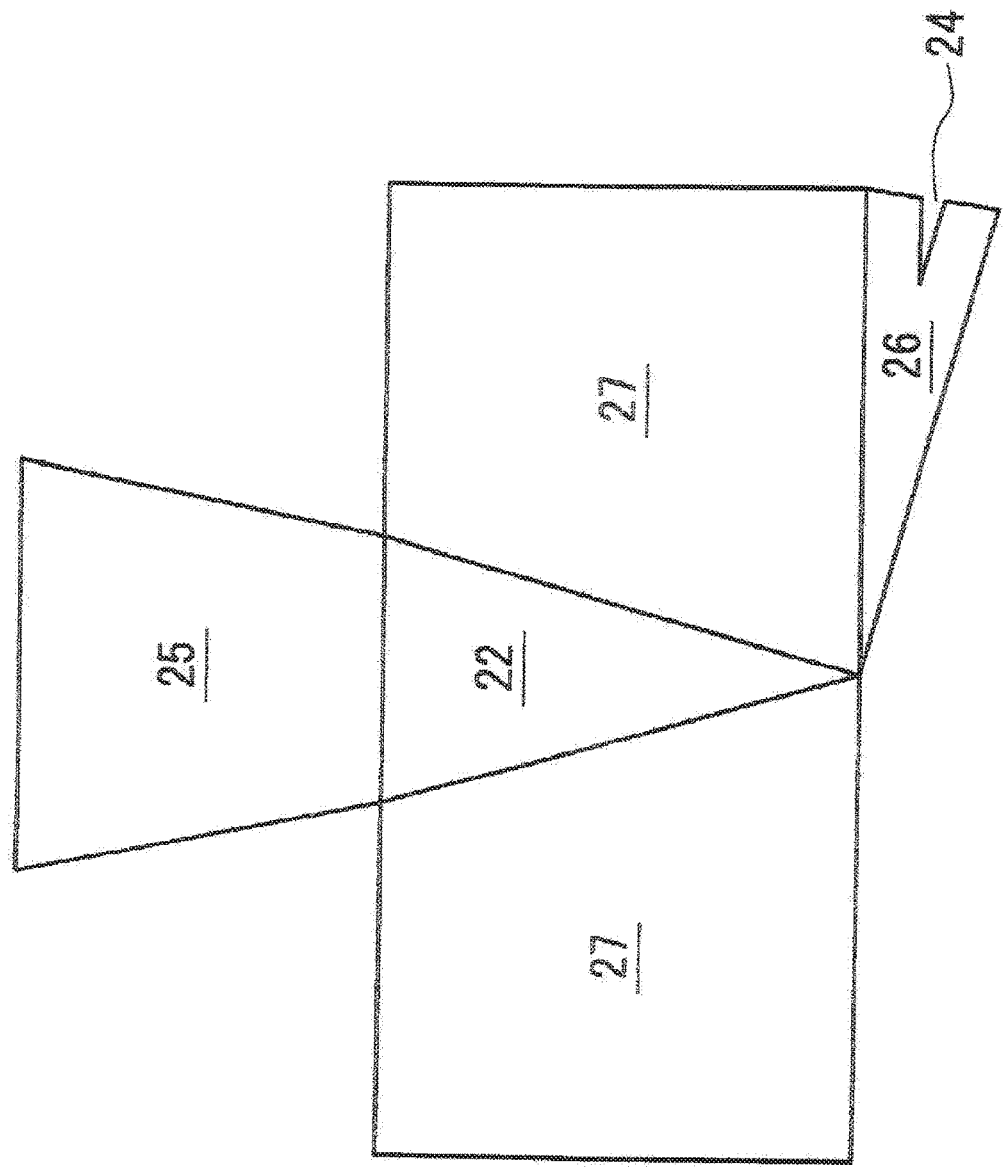
FIG. 5 is a development diagram of the net.

FIG. 3 is a perspective view diagram showing an example of the net. FIG. 4(A) is a diagram showing the net in the plan view, FIG. 4(B) is a diagram showing the net in the front elevation view, and FIG. 4(C) is a diagram showing the net in the side view. FIG. 5 is a development diagram of the net.

The net 2, as has been described above, comprises an opening portion 21 and a bottom portion 22, and a prescribed depth D that separates the opening portion 21 and the bottom portion 22.

In this example, the opening portion 21 exhibits a quadrilateral shape in the plan view, and the bottom portion 22 exhibits the shape of an isosceles triangle in the plan view.

The opening edge portions 21A at the left and right and at the front of the opening portion 21 have been provided with the coupling portion 12 of the frame 1 and the fold back portion 23 for passing through the string body 13. In the fold back portion 23, the frame 1 and the net 2 are coupled by passing the coupling portion 12 and the string body 13. In this state, the gripping portion 11 projects towards the near side of the left and right fold back portions 23. Therefore, in these explanations, the side, at which the gripping portion projects, is called a near side, and the side opposite to that side is called a front side. The two sides seen from the near side may also be called the left and right sides.

The rectangular shape of the opening portion 21 has a trapezoidal shape, in which the side on the near side is shorter than the side on the front side. The isosceles triangle of the bottom portion has an apex 28 on the near side, where the two equal sides meet. The front-side side-surface 25 placed between the left and right side-surfaces 27 has a trapezoidal shape, in which the lower side is shorter than the upper side. The near-side side-surface 26 placed between the left and right side-surfaces 27 has a shape of an isosceles triangle with the apex 28, where the two equal sides meet being placed at the bottom. The near-side side-surface 26 has been formed a V-shaped cut 24 forming an isosceles triangle at the top.

In other words, the bottom portion 22 has a shape that has an apex 28 in the direction towards the gripping portion 11 of the operating frame 10. In this example, this is an isosceles triangle as described above. Further, the opening portion 21 has a shape that has one side in the direction towards the gripping portion 11 of the operating frame 10. In addition, the opening portion 21 has a shape that has one side in the direction towards the tip of the operating frame 10. In this example, this is a trapezoidal shape as has been described above.

Method of Use

With an animal capturing net of the present embodiment, it is possible, for example, to capture an animal as follows. The net 2 is put on the animal from above while gripping respectively the gripping portions 11 of the set of two operating frames 10 with both hands, when the coupling portion 12 is open, and the bottom portion 22 of the net is above. In that state, it is possible to capture an animal by covering the animal with the net 2 by closing the coupling portion 12 by operating the operating frame 10. Also, when an animal hides under a bed or in a carry case because the operating frame 10 can independently operate, the closed operating frame 10 can be inserted in a narrow space such as under a bed or in a carry case. By this operation, a cat can be captured by wrapping with the net.

Figure 6:
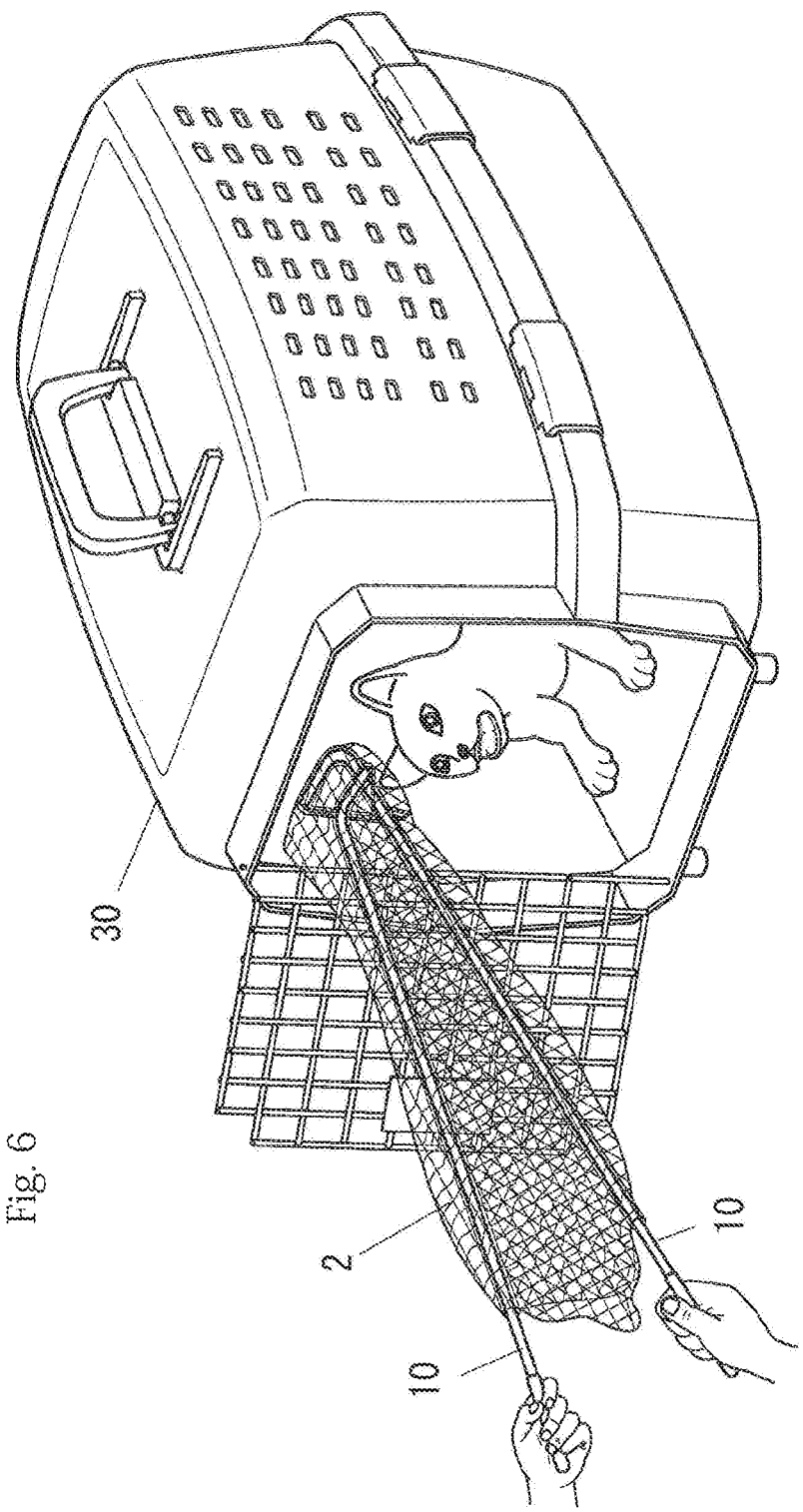
FIG. 6 is a schematic illustration showing the first step of the operation of the present invention.
Figure 7:
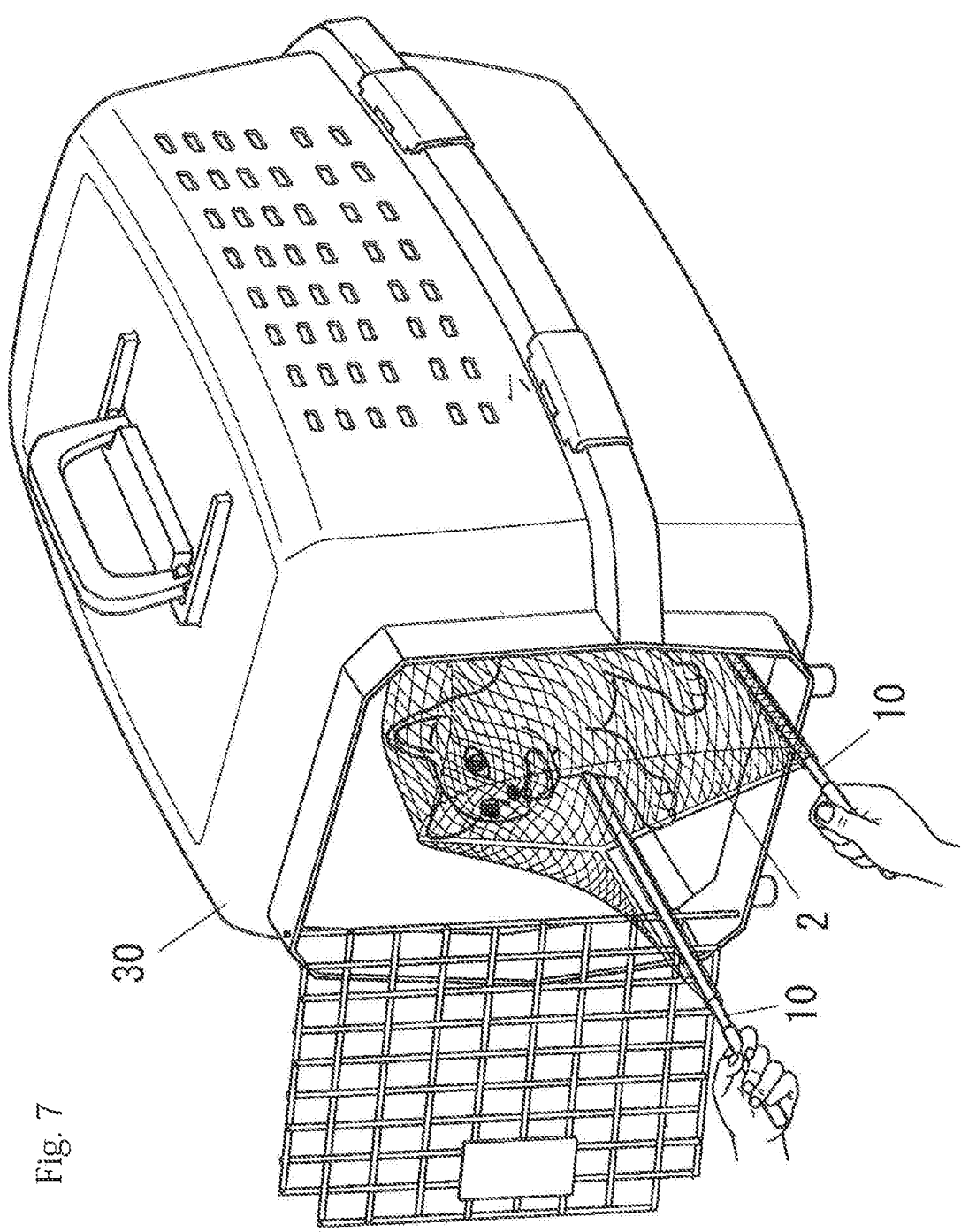
FIG. 7 is a schematic illustration showing the second step of the operation of the present invention.

FIGS. 6 to 9 show an example situation, in which an animal does not come out from a carry case. FIG. 6 is a schematic illustration showing the first step of the operation of the present invention. FIG. 7 is a schematic illustration showing the second step of the operation of the present invention. FIG. 8 is a schematic illustration showing the third step of the operation of the present invention. FIG. 9 is a schematic illustration showing the fourth step of the operation of the present invention. FIG. 10 is a schematic illustration showing another example to stable the animal by the operation of the present invention.

As seen from FIG. 6, when the animal does not come out from the carry case 30, the door of the carry case 30 is opened, and then the closed operating frames 10 are inserted. At this time, regardless of the width of the net and the size of the door of the carry case, the closed operating frames 10 can be inserted because the present invention designed such that the operating frames 10 can be operated independently.

Then, as seen from FIG. 7, the operating frame 10 inside of the carry case 30 is opened, and the animal is covered with the net. After covering the animal, the operating frame 10 is closed, and the animal is captured. When operating the operating frame 10 like this, the hook shape part of the frame can hold the animal's legs and stable the move, thereby making it easy to wrap the animal and capture it. Later, as seem from FIG. 8, while wrapping the animal by the net 2, the animal can be dragged out from the carry case 30.

Then, the animal wrapped by the net 2, as seen from FIG. 9, is carried it out to the examination table by keeping the state. Therefore, for example, when giving an injection to the animal, it is possible to inject it over the net 2 easily.

Also, for example, when examining the oral cavity of the animal, as seen from FIG. 10, the animal can be treated by wrapping the body of the animal and only the head out of the net. In that state, it is easy and safe to carry out examination, blood sample collection, body examination, nail clipping, or the like.

Effect of the Example

The following effect is obtained by the present embodiment.

In an animal capturing net of the present embodiment, since the shape of the opening portion 21 of the net 2 has a side towards the gripping portion 11 of the operating frame 10, it is possible to open and close widely the coupling portion 12, and it is easy to put the net 2 over an animal. Further, the shape of the bottom portion 22 of the net 2 has an apex 28 in the direction towards the gripping portion 11 of the operating frame 10. Because of this, the space for the animal to move becomes small when the net 2 is put over the animal, the movement of the animal is restricted, and the animal can be captured smoothly. Then, after capturing the animal, in the state, in which the opening portion is closed by bringing together the two operating frames 10, if the top and bottom of the net are inverted, it will be possible to restrain that animal as it is. In that state, it is possible to carry out examination, blood sample collection, body examination, nail clipping, or the like. It becomes extremely easy to carry out, for example, examinations or the like by a veterinarian. Also, because the operating frame 10 can independently operate, the closed operating frame 10 can be inserted in a narrow space such as under a bed or in a carry case. It makes capturing an animal by operating the operating frame 10 to wrap an animal with the net is easy and safe.

In an animal capturing net of the present embodiment, the frame 1 has the tips of the coupling portions 12 of the two operating frames 10 respectively formed in the shape of hooks. Because of this, when the net 2 is placed over the animal from the above and the coupling portion 12 is closed, the hook shaped portions get caught with the legs of the animal, thereby stopping the movement of the animal, and it is possible to wrap the animal easily with the net 2 and to capture the animal.

In an animal capturing net of the present embodiment, in the frame 1, the tips of the two operating frames 10 are coupled with each other by a string body 13. Because of this, when the net is put over an animal, the shape of the opening of the net 2 becomes stable along the string body 13, and it is easy to put the net 2 over an animal.

Further, since the string body 13 is made a chain, particularly made of a metal, it becomes easy for the opening portion 21 of the net 2 to widen, and it becomes easy to cover the animal with the net 2 because of the centrifugal force acting on the string body 13 at the time the net 2 is put over the animal.

In addition, the opening portion 21 of the net 2 has a side in the direction towards the tip of the operating frame 10. In this example, this is a rectangle. Since the rectangle is forming a trapezoid with the side at the front being longer than the side that is near, the opening portion 21 on the side that is put over the animal is wide, and it is easy to put the net 2 over the animal. The rectangular shape of the opening portion 21 is a trapezoid with the side that is near is shorter than the side at the front, the near side with the gripping portion 11 has been made narrow, the slackness of the net 2 at the time of operation becomes small, and the operation is easily to be performed. In addition, since the side-surface 25 at the front constitutes a trapezoid with the side at the top being longer than the side at the bottom, the opening portion 21 on the side that is put over the animal is wide, and it is easy to put the net 2 over the animal. Further, by forming a V-shaped cut 24 in the side surface 26 of said near side, the cut 24 becomes wide at the time of operation, and the operation is easily to be performed. Further, since the near-side side-surface 26 has the shape of an isosceles triangle, and since the apex 28 at which the two equal sides meet is placed below, the space, in which the animal can move when the net 2 is put over the animal is small, the movement of the animal is restricted, and it is possible to capture the animal smoothly.

Modified Example

While particularly preferable embodiments of the present invention have been described above, the present invention is not limited to the examples provided above and can be implemented through various types of modifications and the intention of the present invention is to include various modified examples of the present invention.

For example, the operating frame 10 or the string body 13 can be made not only using a metal such as aluminum or the like, but can also be formed from a plastic or the like. Further, the coupling of frame 1 and net 2 can also be done using coupling rings, or the like.

The present invention can of course be used for cats. But the present invention can also be used for small-sized dogs that bite or scratch, and can also be used for other types of animals.

DESCRIPTION OF REFERENCE NUMERALS

1: Frame
2: Net
10: Operating frame
11: Gripping portion
12: Coupling portion
13: String-shaped body
21: Opening portion
21A: Opening edge portion
22: Bottom portion
23: Fold back portion
24: Cut
25: Front-side side-surface
26: Near-side side-surface
27: Left and right side-surfaces
D: Depth

What is claimed is:

1. An animal capturing net comprising:
a net having an upper opening portion, a left side-surface, a right side-surface, a front-side side-surface, a near-side side-surface, a lower bottom portion, and a depth that separates the upper opening portion and the lower bottom portion; and
a frame that is coupled with the net along an opening edge portion at the upper opening portion of the net, the frame including a set of two operating frames, each operating frame of the set of two operating frames having a gripping portion and a coupling portion that extends from the gripping portion and couples with the opening edge portion, wherein
the front-side side-surface is disposed between the left side-surface and the right side-surface, the front-side side-surface having a trapezoidal shape in which a lower side of the front-side side-surface is shorter than an upper side of the front-side side-surface,
the near-side side-surface is disposed between the left side-surface and the right side-surface, the near-side side-surface having an isosceles triangle shape with an apex at which two equal sides of the isosceles triangle shape meet, the apex being at a bottom of the near-side side-surface, the near-side side-surface being located closer to the gripping portion of each operating frame of the set of two operating frames than the front-side side-surface,
the lower bottom portion having another isosceles triangle shape with another apex at which two equal sides of the another isosceles triangle shape meet, the another apex being located closest to the gripping portion of each operating frame of the set of two operating frames than a remainder of the lower bottom portion, and
the apex of the near-side side-surface contacting the another apex of the lower bottom portion.

2. The animal capturing net according to claim 1, wherein each coupling portion of the set of two operating frames respectively has a tip formed in the shape of hooks.

3. The animal capturing net according to claim 1, wherein tips of the set of two operating frames are coupled to each other by a string body.

* * * * *